United States Patent
Tsuruoka et al.

(10) Patent No.: US 9,623,073 B2
(45) Date of Patent: Apr. 18, 2017

(54) LEARNING MOTIVATION IMPROVERS

(71) Applicants: SUNTORY HOLDINGS LIMITED, Osaka (JP); CEREBOS PACIFIC LIMITED, China Square Central (SG)

(72) Inventors: Nobuo Tsuruoka, Osaka (JP); Yoshinori Beppu, Osaka (JP); Hirofumi Kouda, Kanagawa (JP); Hiroshi Watanabe, Tokyo (JP)

(73) Assignees: SUNTORY HOLDINGS LIMITED, Osaka (JP); CEREBOS PACIFIC LIMITED, China Square Central (SG)

( * ) Notice: Subject to any disclaimer, the term of this patent is extended or adjusted under 35 U.S.C. 154(b) by 0 days.

(21) Appl. No.: 14/935,850

(22) Filed: Nov. 9, 2015

(65) Prior Publication Data

US 2016/0058831 A1    Mar. 3, 2016

Related U.S. Application Data

(63) Continuation of application No. 13/965,946, filed on Aug. 13, 2013, now abandoned, which is a continuation of application No. 13/517,109, filed as application No. PCT/JP2010/053594 on Feb. 26, 2010, now abandoned.

(30) Foreign Application Priority Data

Dec. 25, 2009    (JP) .................. 2009-296164

(51) Int. Cl.
| | |
|---|---|
| A61K 38/12 | (2006.01) |
| A23L 1/305 | (2006.01) |
| A23L 2/52 | (2006.01) |
| A61K 9/00 | (2006.01) |
| A61K 31/496 | (2006.01) |
| A61K 31/498 | (2006.01) |
| A23L 33/18 | (2016.01) |

(52) U.S. Cl.
CPC ............... *A61K 38/12* (2013.01); *A23L 2/52* (2013.01); *A23L 33/18* (2016.08); *A61K 9/0053* (2013.01); *A61K 31/496* (2013.01); *A61K 31/498* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 7,202,279 B1 | 4/2007 | Kozikowski et al. | |
| 8,044,103 B2 | 10/2011 | Kozikowski et al. | |
| 2012/0282387 A1 | 11/2012 | Matsubayashi et al. | |
| 2012/0283178 A1 | 11/2012 | Tsuruoka et al. | |
| 2012/0283270 A1 | 11/2012 | Matsubayashi et al. | |
| 2013/0331344 A1 | 12/2013 | Tsuruoka et al. | |

FOREIGN PATENT DOCUMENTS

| | | |
|---|---|---|
| JP | 6172202 | 6/1994 |
| JP | 2000-327575 A | 11/2000 |
| JP | 2002-58450 A | 2/2002 |
| JP | 2003-525850 A | 9/2003 |
| JP | 2007-99660 A | 4/2007 |
| KR | 10-0674604 B1 | 1/2007 |
| WO | 99/40931 A1 | 8/1999 |
| WO | 2007/116987 A1 | 10/2007 |
| WO | 2009/093671 A1 | 7/2009 |

OTHER PUBLICATIONS

International Search Report for International Application No. PCT/JP2010/053594, mail date is May 25, 2010.
International Preliminary Report on Patentability for International Application No. PCT/JP2010/053594, issued Jun. 26, 2012.
Japanese Office Action issued with respect to Japanese Patent Application No. 2011-549842, dated Mar. 16, 2012, along with an English-language translation.
Shi et al., "Studies on Antidepressant Effects of Several Overshort Peptides (OSP)," *Acta Pharmaceutica Sinica*, vol. 26, No. 7, p. 546-547, 1991, along with an English-language translation.
Prasad, Peptides (1995) 16(1), 151-164.
Murakami et al. machine translation of JP6172202.

*Primary Examiner* — Marcela M Cordero Garcia
*Assistant Examiner* — Catherine Mader
(74) *Attorney, Agent, or Firm* — Greenblum & Bernstein, P.L.C.

(57) ABSTRACT

The present invention aims to provide antidepressants which are free from the problem of side effects and are excellent in safety. The present invention also aims to provide learning motivation improvers which are useful for improvement of learning motivation and can be ingested continuously.

The present invention provides antidepressants and learning motivation improvers, each comprising a cyclic dipeptide with the 2,5-diketopiperazine structure as an active ingredient.

11 Claims, 2 Drawing Sheets

LEARNING MOTIVATION IMPROVERS

CROSS-REFERENCE TO RELATED APPLICATIONS

This application is a Continuation of U.S. application Ser. No. 13/965,946, filed Aug. 13, 2013, which is a Continuation of U.S. application Ser. No. 13/517,109, filed Jun. 19, 2012, which is the National Stage of International Application No. PCT/JP2010/053594, filed Feb. 26, 2010, which claims priority to Japanese Application No. JP 2009-296164, filed Dec. 25, 2009. The disclosure of application Ser. Nos. 13/965,946, 13/517,109 and PCT/JP2010/053594 are expressly incorporated by reference herein in their entireties.

TECHNICAL FIELD

The present invention relates to an antidepressant or a learning motivation improver, which comprises a cyclic dipeptide with the 2,5-diketopiperazine structure as an active ingredient.

BACKGROUND ART

In a highly complex modern society, a reduction of willingness turns into a problem. For example, the term "motivation crisis" is used to describe the problem of reduced motivation in young people. Moreover, it is said that depression patients often show symptoms of hypobulia, and there is a demand for the development of drugs capable of improving hypobulia.

Therapeutic or prophylactic agents for depression currently used in clinical cases are tricyclic antidepressants and tetracyclic antidepressants, as well as selective serotonin reuptake inhibitors (hereinafter referred to as "SSRI") and serotonin/noradrenaline reuptake inhibitors (hereinafter referred to as "SNRI"). SSRI and SNRI are antidepressants that are designed to greatly reduce the side effects of conventional tricyclic antidepressants (Journal of clinical and experimental medicine (Igaku no Ayumi), Vol. 219, No. 13, 963-968, 2006). However, although these side effects have been reduced, SSRI and SNRI are reported still to have other side effects.

In terms of safety, there are reports of various therapeutic or prophylactic agents for depression, which comprise a component(s) extracted from naturally occurring products as their active ingredient. For example, a ginkgo leaf extract which is a component extracted from ginkgo leaves (Japanese Patent Public Disclosure No. 2007-99660), a hop extract (Japanese Patent Public Disclosure No. 2002-58450) and so on are reported, but it is difficult to consider that these extracts have established safety because their starting materials are not usually ingested and people have little experience in eating them.

On the other hand, cyclic dipeptides including 2,5-diketopiperazine ring compounds are known to have various physiological activities, and it is expected that such dipeptides will grow in demand in the medical and pharmacological fields. Dipeptides can be designed to have additional physical properties and/or new functions, which cannot be seen in single amino acids, and hence they are expected to be applicable to a wider range than that of amino acids. Moreover, dipeptides are also known to have additional physical properties and/or new functions, depending on their structural differences, e.g., whether they are linear or cyclic.

As for cyclic dipeptides, reports as described below have been issued. For example, some reports have shown that pyrrolo[1,2-a]pyrazine-1,4-dione,hexahydro-3-(1-methylethyl)-,(3S,8aS) and pyrrolo[1,2-a]pyrazine-1,4-dione,hexahydro-3-(2-methylpropyl)-,(3S,8aS), which are generated in roasted cocoa (J. Agric. Food Chem. 2005, 53, 7222-7231) or in coffee (J. Agric. Food Chem. 2000, 48, 3528-3532), serve as bitter components, and that 21 types of cyclic dipeptides are generated from a heat-treated product of chicken meat (Eur. Food Res. Technol. (2004) 218:589-597). In addition, other reports have shown that 2,5-piperazinedione,3,6-bis(1H-indol-3-ylmethyl)-,(3S,6S) and pyrrolo[1,2-a]pyrazine-1,4-dione,hexahydro-3-(phenylmethyl)-,(3S,8aS) have an anticancer effect (J. Pharm Pharmacol. 2000 January; 52(1):75-82); pyrrolo[1,2-a]pyrazine-1,4-dione,hexahydro-3-(1H-indol-3-ylmethyl)-,(3S,8aS) and pyrrolo[1,2-a]pyrazine-1,4-dione,hexahydro-3-(phenylmethyl)-,(3S,8aS) have an antibacterial effect; and pyrrolo[1,2-a]pyrazine-1,4-dione,hexahydro-3-(1H-indol-3-ylmethyl)-,(3S,8aS) and 2,5-piperazinedione,3,6-bis(1H-indol-3-ylmethyl)-,(3S,6S) have an antifungal effect (Pharmazie 1999 October; 54(10):772-5). However, it has not been reported that cyclic dipeptides are useful for treatment and/or prevention of depression, or that cyclic dipeptides have an improving effect on learning motivation.

SUMMARY OF INVENTION

Technical Problem

The present invention aims to provide antidepressants which are free from the problem of side effects and are excellent in safety. The present invention also aims to provide learning motivation improvers which are useful for improvement of learning motivation and can be ingested continuously.

Solution to Problem

As a result of extensive and intensive efforts made to solve the problems stated above, the inventors of the present invention have found that components having SSRI or SNRI activity and components having an improving effect on learning motivation are contained in chicken extract. The inventors have further identified these active ingredients to be cyclic dipeptides with the 2,5-diketopiperazine structure. These findings led to the completion of the present invention.

Namely, the present invention is directed to [1] to [8] shown below.

[1] An antidepressant comprising a cyclic dipeptide with the 2,5-diketopiperazine structure as an active ingredient.

[2] The antidepressant according to [1] above, wherein the cyclic dipeptide is one or more members selected from the group consisting of 2,5-piperazinedione,3,6-bis(phenylmethyl)-,(3S,6S), pyrrolo[1,2-a]pyrazine-1,4-dione,hexahydro-3-(1H-imidazol-4-ylmethyl)-,(3S,8aS), and pyrrolo[1,2-a]pyrazine-1,4-dione,hexahydro-3-(1H-indol-3-ylmethyl)-,(3S,8aS).

[3] The antidepressant according to [2] above, which further comprises one or more members selected from the group consisting of 2,5-piperazinedione,3,6-bis(1H-indol-3-ylmethyl)-,(3S,6S), pyrrolo[1,2-a]pyrazine-1,4-dione,hexahydro-3-(2-methylpropyl)-, (3S,8aS), and pyrrolo[1,2-a]pyrazine-1,4-dione,hexahydro-3-(1-methylethyl)-,(3S,8aS).

[4] The antidepressant according to any one of [1] to [3] above, which is for oral administration.

[5] The antidepressant according to any one of [1] to [4] above, which is a prophylactic and/or therapeutic agent for depression, senile depression symptoms, depressed mood, hypobulia, anxiety, or insomnia or anorexia associated with these symptoms.

[6] A learning motivation improver comprising a cyclic dipeptide with the 2,5-diketopiperazine structure as an active ingredient.

[7] The learning motivation improver according to [6] above, wherein the cyclic dipeptide is 2,5-piperazinedione, 3,6-bis(phenylmethyl)-,(3S,6S).

[8] The learning motivation improver according to [6] or [7] above, which is for oral administration.

Advantageous Effects of Invention

The present invention provides antidepressants and learning motivation improvers, which have SSRI activity or SNRI activity. The antidepressants and learning motivation improvers of the present invention are not only excellent in their effects, but are also extremely safe, and are further suitable for use in foods and beverages because they are tasteless and odorless and have a white color in purified form.

DESCRIPTION OF EMBODIMENTS

Figure 1:
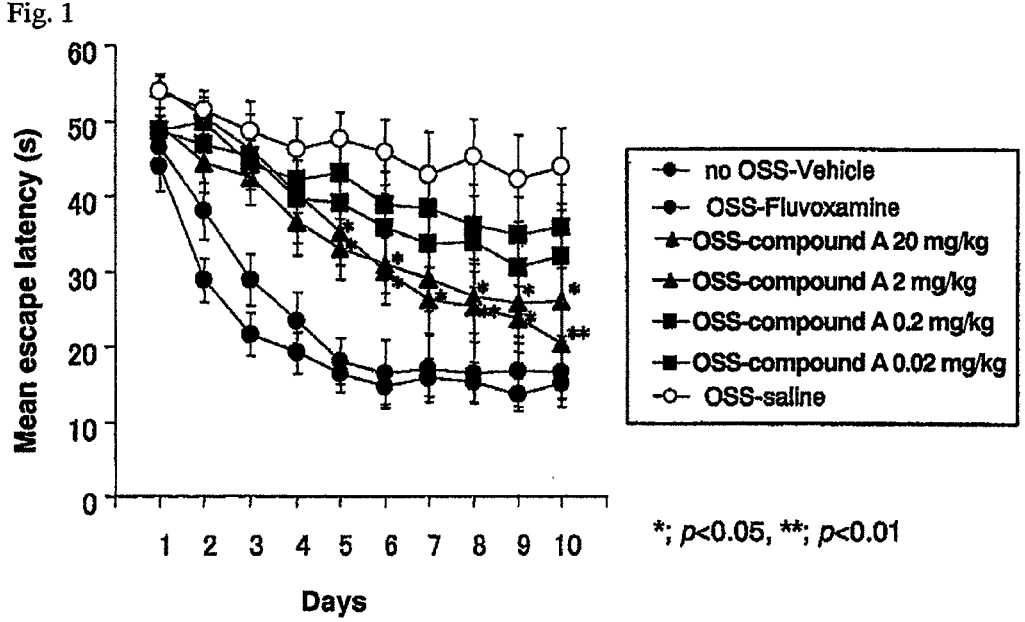
FIG. 1 shows the test results of whether the ingestion of a test sample reduces the time required for mice to reach an escape platform (escape latency) when repeating the test.

A detailed explanation will be given below for the embodiments of the present invention.

The present invention is directed to an antidepressant or a learning motivation improver, which comprises a cyclic dipeptide with the 2,5-diketopiperazine structure as an active ingredient.

The term "antidepressant" as used herein is intended to mean an agent having a prophylactic and/or therapeutic effect on depression, senile depression symptoms, depressed mood, hypobulia (e.g., reduced willingness to live, reduced learning motivation), anxiety, or insomnia or anorexia associated with these symptoms.

In particular, 2,5-piperazinedione,3,6-bis(phenylmethyl)-, (3S,6S) (CA Registry Number: 2862-51-3) (hereinafter referred to as "compound A"), pyrrolo[1,2-a]pyrazine-1,4-dione,hexahydro-3-(1H-imidazol-4-ylmethyl)-,(3S,8aS) (CA Registry Number: 53109-32-3) (hereinafter referred to as "compound B") and pyrrolo[1,2-a]pyrazine-1,4-dione, hexahydro-3-(1H-indol-3-ylmethyl)-,(3S,8aS) (CA Registry Number: 38136-70-8) (hereinafter referred to as "compound C") have inhibitory activity on serotonin transporter binding, while 2,5-piperazinedione,3,6-bis(1H-indol-3-ylmethyl)-,(3S,6S) (CA Registry Number: 20829-55-4) (hereinafter referred to as "compound D"), pyrrolo[1,2-a]pyrazine-1,4-dione,hexahydro-3-(2-methylpropyl)-,(3S,8aS) (CA Registry Number: 2873-36-1) (hereinafter referred to as "compound E") and pyrrolo[1,2-a]pyrazine-1,4-dione, hexahydro-3-(1-methylethyl)-,(3S,8aS) (CA Registry Number: 2854-40-2) (hereinafter referred to as "compound F") have inhibitory activity on norepinephrine transporter binding. The former are useful as SSRI antidepressants, and the latter are useful as SNRI antidepressants when combined with any one of the former.

Among them, compound A showed no toxicity in a single-dose (acute) toxicity study in mice even when administered at 2 g/kg, and its maximum no-effect dose was 2 g/kg/day or more in a 28-day repeated dose toxicity study in rats. Moreover, in genetic toxicity studies (i.e., Ames test, chromosomal aberration test, and mouse micronucleus test), compound A shows no mutagenicity, and hence it is an antidepressant extremely excellent in safety.

As used herein, the term "SSRI antidepressant" is intended to mean an agent that selectively binds to the serotonin transporter and inhibits the reuptake of serotonin through this serotonin transporter. Inhibitory activity on serotonin transporter binding may be measured, for example, as described in Eur. J. Pharmacol., 368: 277-283, 1999. Namely, it is measured by determining whether $^3$H-labeled imipramine binds to the human serotonin transporter expressed in CHO cells. The concentration ($IC_{50}$) of compound A required for 50% inhibition of serotonin transporter binding is 8.1 µM.

The term "SNRI antidepressant" is intended to mean an agent that binds to both serotonin and norepinephrine transporters, and inhibits the reuptake of serotonin and norepinephrine. Inhibitory activity on norepinephrine transporter binding may be measured, for example, as described in Nature, 350: 350-354, 1991. Namely, it is measured by determining whether $^3$H-labeled nisoxetine binds to the human norepinephrine transporter expressed in CHO cells.

On the other hand, the Morris water maze test has been reported as a method for measuring spatial memory and learning (Learn. Motiv. 12, 239-260 (1981)). In this test, the time required to reach an escape platform (escape latency) is used as a parameter for evaluation, because mice will remember their surrounding scenery and swim in a pool filled with water to try to find and reach the escape platform, which is a goal, with their memory as a guide. Since mice to be used in this test are treated to reduce their motivation by being allowed to swim in a pool having no escape platform before the Morris water maze test, a reduction in the time required to reach the escape platform can be regarded as an improvement in learning motivation.

Active ingredients including compound A, which are cyclic dipeptides with the 2,5-diketopiperazine structure, may be commercially available synthetic reagents, but the ingredients extracted from naturally occurring products are more preferred for use in terms of safety. To obtain compound A or the like from naturally occurring products, a process comprising the following steps can be presented as an example:

(1) a pretreatment step in which meat of livestock or poultry, fish meat or shellfish meat is used as a starting material and heated in a liquid to remove water-soluble proteins contained therein;

(2) a heating step in which the liquid is replaced after the pretreatment and heating is repeated again; and (3) a filtration step in which the obtained liquid sample is filtered.

A preferred starting material used in the above pretreatment step (1) is a naturally occurring product rich in useful components, i.e., cyclic dipeptides with the 2,5-diketopiperazine structure including compound A, particularly meat of livestock or poultry, fish meat, or shellfish meat. Examples of meat of livestock or poultry include meat of livestock, i.e., cattle, pig, horse, sheep or goat, meat of non-livestock animals such as wild boar or deer, meat of poultry, i.e., chicken, turkey, quail, domestic duck or crossbred duck, as well as meat of non-poultry wild birds such as wild duck, pheasant, sparrow or thrush. Likewise, it is also possible to use fish meat and shellfish meat which are eaten in the course of a normal diet. As other examples, plant materials such as coffee and cocoa can also be used. Among these examples for meat of livestock or poultry, fish meat and shellfish meat, chicken meat is preferred for use because compound A and so on can be efficiently obtained at high concentrations.

Although the reason why compound A is obtained in large amounts when using chicken meat is unknown, it is inferred that proteins in chicken meat are rich in the contiguous phenylalanine (-Phe-Phe-) structure and thereby generate a dipeptide (Phe-Phe) in abundance, as a result of which compound A of interest will be obtained in large amounts.

In the pretreatment step (1), any treatment for reducing water-soluble proteins contained in meat of livestock may be performed, for example, by boiling in water at 100° C. to 160° C. for 30 minutes to several hours (preferably about 3 to 8 hours, more preferably about 3 to 4 hours). As a heating device, a pressure cooker, an autoclave and so on can be combined for use depending on the intended conditions.

The heating step (2) is preferably accomplished at a high temperature under a high pressure (100° C. or more and 1 atm or more), for example, at 100° C. or more, and more preferably at 125° C. or more. As a heating device, a pressure cooker, an autoclave and so on can also be combined for use depending on the intended conditions.

The pretreatment step (1) and the heating step (2) may be performed continuously as a single step without liquid replacement. Alternatively, the pretreatment step may be followed by removal of the starting material and then replacement of the liquid before the starting material is subjected to the heating step. Since samples with lower Brix values can be obtained when liquid replacement is performed after the pretreatment step (1) and before the heating step (2), it is more desirable to use liquid replacement.

It should be noted that heat treatment in the steps (1) and (2) is preferably performed in a solvent in order to prevent plant and animal materials from burning. Examples of a solvent preferred for use include water, ethanol, or mixtures thereof. Namely, a plant or animal material containing proteins (preferably proteins rich in the contiguous phenylalanine (-Phe-Phe-) structure) is mixed with a solvent and subjected to heat treatment, followed by collection of the solvent to obtain a solution rich in compound A. It should be noted that the concentration of compound A can be quantified in various manners, for example, by high performance liquid chromatography (HPLC).

The resulting solution containing cyclic dipeptides with the 2,5-diketopiperazine structure including compound A may be used directly as the agent of the present invention or, if necessary, may be purified or concentrated to further increase the concentrations of the active ingredients. Concentration may be accomplished by using an evaporator or by lyophilization, etc.

In the filtration step, the power of filtration may be determined as appropriate, depending on the form of the agent, and the filtration step may be accomplished in a manner well known to those skilled in the art.

The antidepressant and learning motivation improver of the present invention may be supplemented as appropriate with additives such as carriers, excipients, stabilizers, antioxidants, antiseptics, surfactants, etc. The precise dosage may be determined as appropriate, depending on the severity of disease, age, sex, body weight and so on. In the case of humans, for example, the active ingredient is given several times a day at a dose of 0.002 to 20 mg/kg per administration. It is preferably given one to three times a day, but the period of administration is not limited in any way.

Although the route of administration may be oral or parenteral, oral dosage forms are preferred in terms of easy administration. Oral dosage forms may be in any form including tablets, capsules, powders, granules, solutions, elixirs, etc. Moreover, in the case of oral dosage forms, the active ingredient is generally formulated into the intended form such as tablets with or without excipients. Examples of excipients used for this purpose include gelatin, saccharides (e.g., lactose, glucose), starches (e.g., wheat starch, rice starch, corn starch), fatty acid salts (e.g., calcium stearate, magnesium stearate), talc, vegetable oils, alcohols (e.g., stearyl alcohol, benzyl alcohol), gum, polyalkylene glycols, etc.

Oral dosage forms comprise the active ingredient of the present invention at a content of 0.01% to 80% by weight, preferably 0.01% to 60% by weight. In the case of solutions, suspensions or syrups comprising the active ingredient of the present invention at a content of 0.01% to 20% by weight can be presented as examples. Carriers used in this case are water-soluble excipients such as flavorings, syrups, pharmaceutical micelles and the like.

The present invention will be further described in more detail by way of the following examples, which are not intended to limit the present invention.

EXAMPLES

Example 1

Measurement of Various Cyclic Peptides for their Inhibitory Activity on Transporter Binding Various cyclic dipeptides were measured for their inhibitory activity on serotonin transporter binding and norepinephrine transporter binding, as described in the prior documents mentioned above (Eur J Pharmacol, 368, 277-283, 1999 for inhibitory activity on serotonin transporter binding; and Nature, 350, 350-354, 1991 for inhibitory activity on noradrenaline transporter binding). Compound C was synthesized by Peptide Institute, Inc., Japan, and the other cyclic dipeptides were purchased from Bachem AG (Bubendorf, Switzerland). The results were expressed as $IC_{50}$ values, i.e., the concentrations of the various cyclic peptides required for 50% inhibition of binding to each transporter (Table 1).

TABLE 1

| Compounds | $IC_{50}$ (µg/ml) |
| --- | --- |
| | Serotonin transporter |
| Compound A | 2.4 |
| Compound B | 580 |
| Compound C | 1060 |
| | Norepinephrine transporter |
| Compound D | 55 |
| Compound E | 420 |
| Compound F | 2100 |

Example 2

Improving Effect on Learning Motivation (1)

Compound A was evaluated for its antidepressive effect and enhancing effect on learning motivation by the method known in the art, i.e., Morris Water Maze (MWM).

First, water which had been colored black with Indian ink was filled into a cylindrical tank of 90 cm diameter and 35 cm height to give a water depth of 20 cm, and the water temperature was set to 22±1° C. To this tank, C57BL/6 mice (male, 9 weeks of age) were each transferred and allowed to experience open space swimming (OSS). Upon OSS, mice will cause changes in their behavior and enter a state corresponding to depression. After repeating OSS for 5 days, the mice were divided into 7 groups.

Next, in the above cylindrical tank of 90 cm diameter and 35 cm height, an escape platform of 10 cm diameter was placed at a water depth of 0.5 cm. The above 7 groups of mice were each orally administered with compound A (Bachem AG (Bubendorf, Switzerland)) or with a comparative drug, fluvoxamine maleate, in the form of a suspension in physiological saline. After 60 minutes, each mouse was transferred to the tank provided with the escape platform, and measured for the time required to find out the invisible escape platform placed below the water surface (i.e., escape latency) to evaluate the spatial memory and learning ability of each mouse (MWM). As control mice, animals experiencing no OSS were administered with physiological saline and subjected to MWM. MWM was repeated five times a day for 10 days.

The results obtained are shown in FIG. 1. As can be seen from FIG. 1, in the mice experiencing no OSS (no OSS—Vehicle), the escape latency was reduced when repeating the test, whereas the mice experiencing OSS showed reduced learning motivation and there was no reduction in the escape latency (OSS—Saline). In contrast, the group receiving compound A showed a dose-dependent reduction in the escape latency. In the 0.02 mg/kg group, the escape latency at 10 days of MWM was reduced by around 20%, when compared to the control group (OSS—Saline) in which animals experiencing OSS were administered with physiological saline. Moreover, in the 20 mg/kg group, the time required to reach the escape platform at 10 days of MWM was substantially the same as that of the group (OSS—Fluvoxamine) receiving fluvoxamine maleate, which is frequently used as SSRI. This indicates that compound A has an enhancing effect on learning motivation.

Example 3

Improving Effect on Learning Motivation (2)

In the same manner as shown in Example 2, mice were administered with 20 mg/kg compound A and then subjected to the MWM test. As a control, a linear dipeptide (Phe-Phe) was administered at 20 mg/kg, followed by the MWM test.

Figure 2:
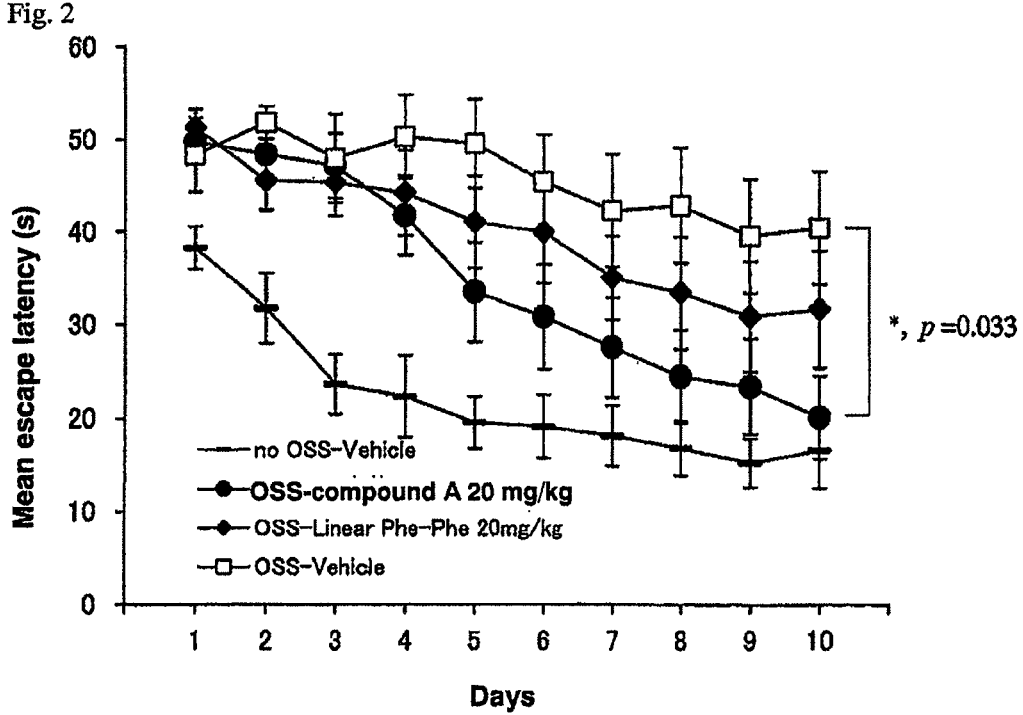
FIG. 2 shows the test results of whether the ingestion of a test sample reduces the time required for mice to reach an escape platform (escape latency) when repeating the test.

The results obtained are shown in FIG. 2. As can be seen from FIG. 2, the linear dipeptide (Phe-Phe) was not confirmed to have a significant effect, whereas compound A showed a significant improving effect on learning motivation over the control group (OSS—Vehicle). Namely, it is indicated that the cyclic dipeptide structure is required for exerting an improving effect on learning motivation.

Example 4

Improving Effect on Learning Motivation (3)

In the same manner as shown in Example 2, another group receiving 0.002 mg/kg administration was prepared and subjected to the same MWM test.

Figure 3:
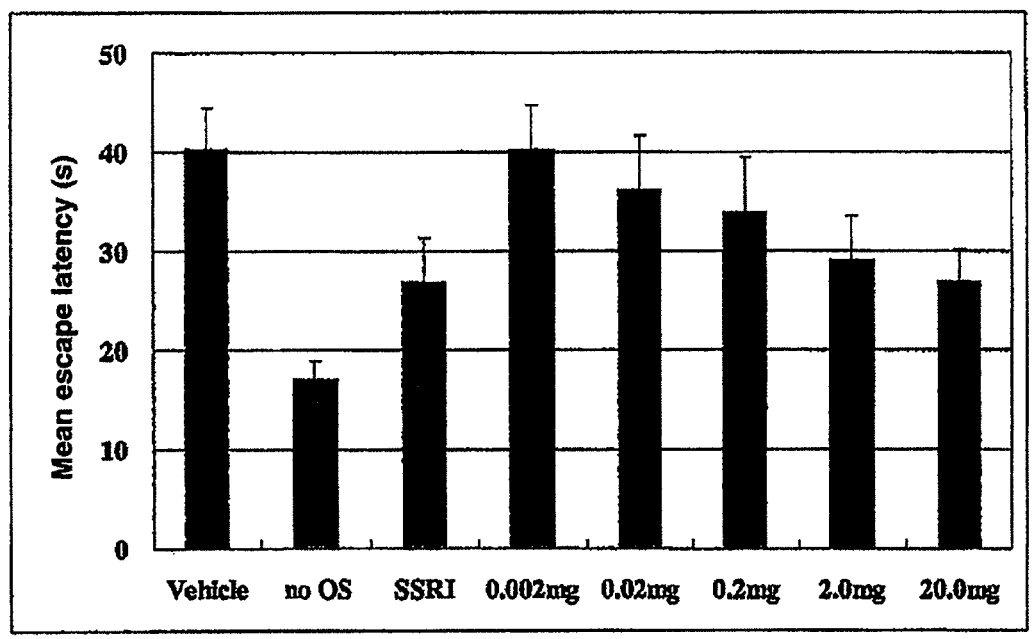
FIG. 3 shows the test results of whether the ingestion of a test sample reduces the time required for mice to reach an escape platform (escape latency) when repeating the test.

The time required to reach the escape platform at 7 days of MWM is shown in FIG. 3 for each group. Compound A was confirmed to exert its effect when administered at 0.02 mg/kg or more. In a case where the dose for humans is predicted from the effective dose in animals, the human dose is calculated to be 1/10 of the mouse dose with a coefficient of 10 based on animal species specificity (Safety Assessment of Foods, edited by Kageaki Aibara and Mitsuru Uchiyama, Japan Scientific Societies Press, 1987). Thus, 0.02 mg/kg which was effective in the above test corresponds to 0.1 mg/human (50 kg). If compound A-containing foods are prepared in the form of beverages and their volume is set to 100 ml, their effective concentration is calculated to be 1.0 µg/ml.

INDUSTRIAL APPLICABILITY

The present invention provides antidepressants and learning motivation improvers, which have SSRI activity or SNRI activity. The antidepressants and learning motivation improvers of the present invention are not only excellent in their effects, but are also extremely safe, and are further suitable for use in foods and beverages because they are tasteless and odorless and have a white color in purified form.

What is claimed is:

1. A method of treating depression comprising administering an effective amount of 2,5-piperazinedione,3,6-bis(phenylmethyl)-,(3S,6S) to a subject in recognized need thereof.

2. The method according to claim 1, wherein the administration is oral administration.

3. The method according to claim 1, wherein the 2,5-piperazinedione,3,6-bis(phenylmethyl)-,(3S,6S) is present in a food, beverage, tablet, capsule, powder, granule, solution, or elixir.

4. The method according to claim 1, wherein the 2,5-piperazinedione,3,6-bis(phenylmethyl)-,(3S,6S) is administered as a prophylactic and/or therapeutic agent for treatment of depression, senile depression symptoms, depressed mood, hypobulia, anxiety, or insomnia or anorexia associated with these symptoms.

5. A method of treating depression comprising administering an antidepressant comprising an effective amount of 2,5-piperazinedione,3,6-bis(phenylmethyl)-,(3S,6S) to a subject in recognized need thereof.

6. The method according to claim 5, wherein the administration is oral administration.

7. The method according to claim 5, wherein the antidepressant is present in a food, beverage, tablet, capsule, powder, granule, solution, or elixir.

8. The method according to claim 5, wherein the antidepressant is administered as a prophylactic and/or therapeutic agent for treatment of depression, senile depression symptoms, depressed mood, hypobulia, anxiety, or insomnia or anorexia associated with these symptoms.

9. A method for improving learning motivation comprising administering an effective amount of 2,5-piperazinedione,3,6-bis(phenylmethyl)-,(3S,6S) to a subject in recognized need thereof.

10. The method according to claim 9, wherein the administration is oral administration.

11. The method according to claim 9, wherein the 2,5-piperazinedione,3,6-bis(phenylmethyl)-,(3S,6S) is present in a food, beverage, tablet, capsule, powder, granule, solution, or elixir.

\* \* \* \* \*

UNITED STATES PATENT AND TRADEMARK OFFICE
CERTIFICATE OF CORRECTION

PATENT NO. : 9,623,073 B2  
APPLICATION NO. : 14/935850  
DATED : April 18, 2017  
INVENTOR(S) : N. Tsuruoka et al.

Page 1 of 1

It is certified that error appears in the above-identified patent and that said Letters Patent is hereby corrected as shown below:

In the Claims

At Column 8, Lines 56-57 (Claim 7, Lines 1-2) please change "the antidepressent" to -- the antidepressant --.

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*